(12) United States Patent
Biedermann et al.

(10) Patent No.: US 11,617,608 B2
(45) Date of Patent: Apr. 4, 2023

(54) COUPLING ASSEMBLY FOR COUPLING A ROD TO A BONE ANCHORING ELEMENT, AND POLYAXIAL BONE ANCHORING DEVICE

(71) Applicant: BIEDERMANN TECHNOLOGIES GMBH & CO. KG, Donaueschingen (DE)

(72) Inventors: Lutz Biedermann, VS-Villingen (DE); Achim Schünemann, VS-Mühlhausen (DE); Dimosthenis Dandanopoulos, VS-Schwenningen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 216 days.

(21) Appl. No.: 16/905,313

(22) Filed: Jun. 18, 2020

(65) Prior Publication Data

US 2020/0383713 A1   Dec. 10, 2020

Related U.S. Application Data

(63) Continuation of application No. 16/042,449, filed on Jul. 23, 2018, now Pat. No. 10,716,609, which is a (Continued)

(30) Foreign Application Priority Data

Jan. 13, 2014   (EP) .................... 14151004

(51) Int. Cl.
*A61B 17/86* (2006.01)
*A61B 17/70* (2006.01)

(52) U.S. Cl.
CPC ...... *A61B 17/8605* (2013.01); *A61B 17/7035* (2013.01); *A61B 17/7037* (2013.01); *A61B 2560/0443* (2013.01)

(58) Field of Classification Search
CPC ..................... A61B 17/7035; A61B 17/7037
See application file for complete search history.

(56) References Cited

U.S. PATENT DOCUMENTS

| 5,716,356 A | 2/1998 | Biedermann et al. |
| 8,075,603 B2 | 12/2011 | Hammill et al. |
| (Continued) | | |

FOREIGN PATENT DOCUMENTS

| EP | 2 221 012 A1 | 8/2010 |
| JP | 2010-194309 A | 9/2010 |
| (Continued) | | |

OTHER PUBLICATIONS

Extended European Search Report issued by the EPO for EP 14151004.0 dated May 27, 2014 (4 pages).

*Primary Examiner* — Nicholas W Woodall
(74) *Attorney, Agent, or Firm* — Lewis Roca Rothgerber Christie LLP

(57) ABSTRACT

A coupling assembly for coupling a rod to a bone anchoring element includes a receiving part having a first end, a second end, a recess having a bottom for receiving the rod, and an accommodation space having an opening at the second end of the receiving part for accommodating a head of the bone anchoring element, and a retainer element configured to be inserted into the receiving part from the first end and to hold at least part of the head, the retainer element having a first portion and a spring portion compressible in an axial direction attached to the first portion. When the retainer element is in the accommodation space in a first position, the spring portion extends in the axial direction from the first portion of the retainer element to an axial position between the first end of the receiving part and the bottom of the recess.

20 Claims, 14 Drawing Sheets

Related U.S. Application Data continuation of application No. 14/596,170, filed on Jan. 13, 2015, now Pat. No. 10,058,367.

(60) Provisional application No. 61/926,691, filed on Jan. 13, 2014.

(56) References Cited

U.S. PATENT DOCUMENTS

| | | | |
|---|---|---|---|
| 8,088,152 B2 | 1/2012 | Schumacher | |
| 9,364,266 B2 | 6/2016 | Biedermann et al. | |
| 2005/0154391 A1* | 7/2005 | Doherty | A61B 17/7038 606/328 |
| 2010/0030279 A1 | 2/2010 | Flynn et al. | |
| 2010/0125302 A1 | 5/2010 | Hammill, Sr. et al. | |
| 2011/0040336 A1 | 2/2011 | Hammill, Sr. et al. | |
| 2012/0046699 A1 | 2/2012 | Jones et al. | |
| 2012/0232598 A1* | 9/2012 | Hestad | A61B 17/7037 29/446 |
| 2012/0253408 A1 | 10/2012 | Timm | |
| 2013/0096622 A1 | 4/2013 | Biedermann et al. | |
| 2013/0150852 A1 | 6/2013 | Shluzas et al. | |
| 2013/0338721 A1 | 12/2013 | Biedermann et al. | |
| 2015/0201972 A1* | 7/2015 | Doubler | A61B 17/7002 606/266 |

FOREIGN PATENT DOCUMENTS

| | | |
|---|---|---|
| JP | 2013-039370 A | 2/2013 |
| JP | 2013-536022 A | 9/2013 |
| WO | WO/2012/030712 | 3/2012 |

* cited by examiner

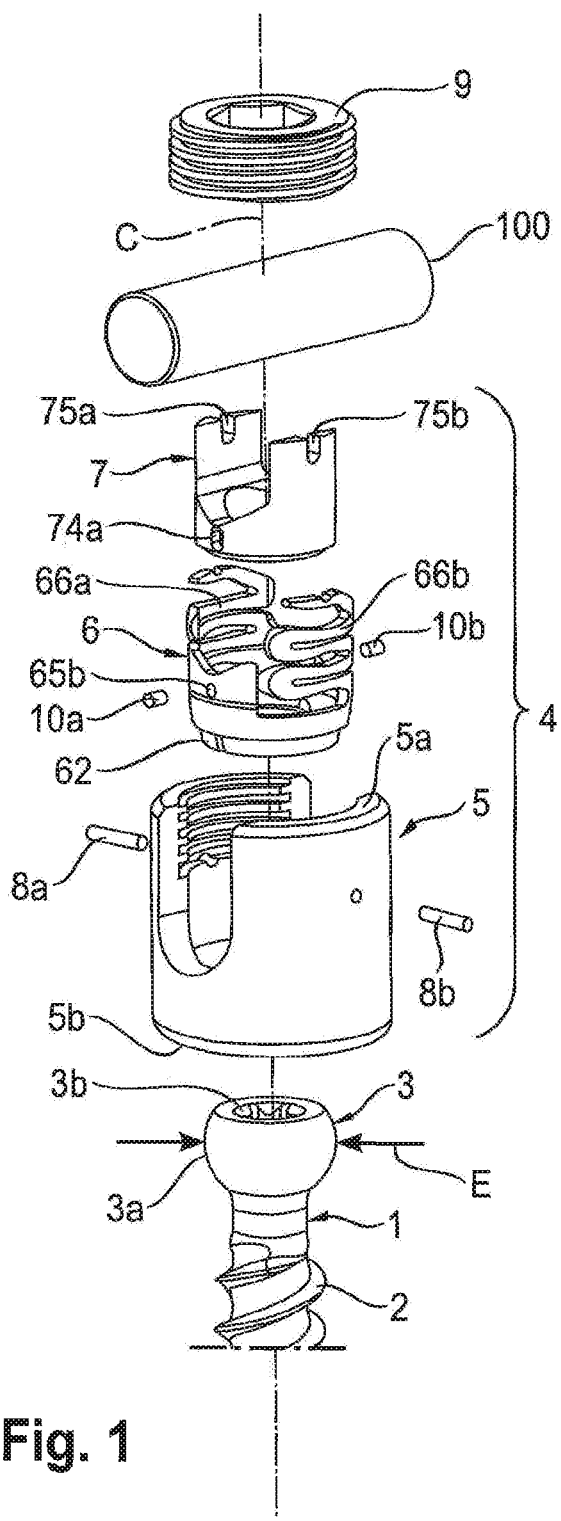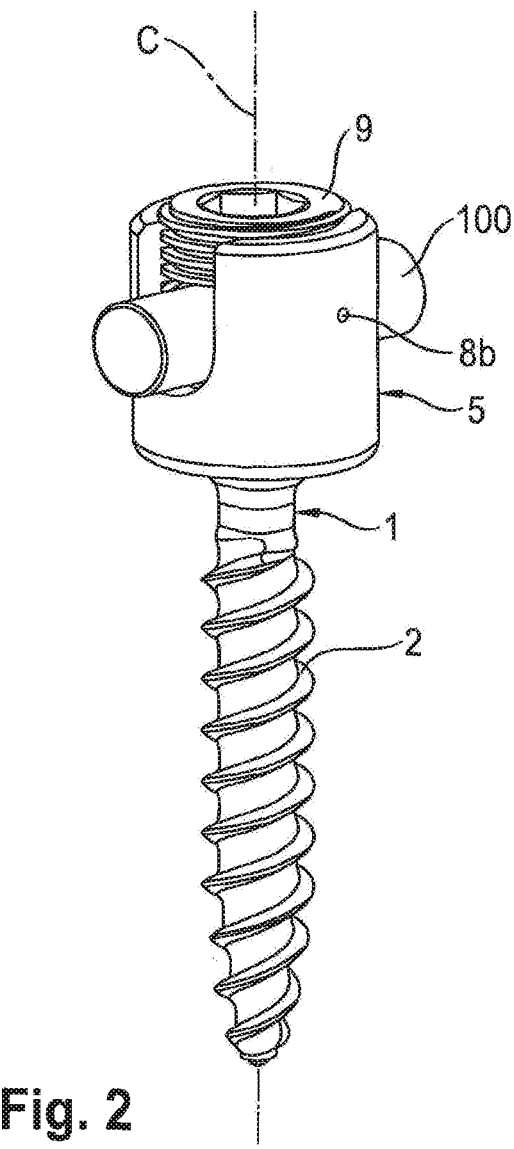
Fig. 1
Fig. 2

COUPLING ASSEMBLY FOR COUPLING A ROD TO A BONE ANCHORING ELEMENT, AND POLYAXIAL BONE ANCHORING DEVICE

CROSS-REFERENCE TO RELATED APPLICATIONS

This application is a continuation of U.S. patent application Ser. No. 16/042,449, filed Jul. 23, 2018, which is a continuation of U.S. patent application Ser. No. 14/596,170, filed Jan. 13, 2015, now U.S. Pat. No. 10,058,367, which claims the benefit of U.S. Provisional Patent Application Ser. No. 61/926,691, filed Jan. 13, 2014, the contents of which are hereby incorporated by reference in their entirety, and claims priority from European Patent Application EP 14151004.0, filed Jan. 13, 2014, the contents of which are hereby incorporated by reference in their entirety.

BACKGROUND

Field

The invention relates to a coupling assembly for coupling a rod to a bone anchoring element, and to a polyaxial bone anchoring device with such a coupling assembly. The coupling assembly includes a receiving part with a channel for receiving the rod, an accommodation space for accommodating a head of a bone anchoring element, and a retainer element for retaining the head of the bone anchoring element in the receiving part. The retainer element has a structure that includes a spring portion that is biased in such a manner that the retainer element snaps automatically onto a head of the bone anchoring element when the head is being inserted.

Description of Related Art

From US 2013/0150852 A1, a polyaxial bone anchor including a housing, a bone screw, and a retainer for pivotably coupling the head of the bone screw to the housing is known. The retainer is positioned into the bore of the housing and includes a plurality of alternating tabs and slots circumferentially arranged to define a cavity for receiving the head portion of the bone screw therein. The bone anchor further includes a resilient spring means biasing the retainer towards the lower end of the housing. The head portion of the bone screw may apply a force against the retainer opposing and overcoming the biasing force of the resilient spring means. The resilient spring means may be, for example, a wave washer, a helical spring, an elastomeric member, etc. or may be circumferential or helical slots formed in the retainer.

U.S. Pat. No. 8,075,603 B2 describes a fastening system consisting of a polyaxial ball and socket joint used in conjunction with a bone screw having threads on one end and a spherical connector on the other end operating as a pivot point about which a connection assembly moves in a polyaxial fashion. A substantially U-shaped connecting assembly has a lower receptacle that operates as a socket for housing an upper retainer ring and a lower split retainer ring. The socket is receptive to the spherical connector which is inserted through the lower split retainer ring causing a momentary displacement thereof which allows for the positioning of the spherical connector between the upper and lower retainer rings. A resilient component positioned between the upper retainer ring and the connecting assembly permits relative predetermined placement and retention of the spherical connector relative to the connector assembly.

SUMMARY

The above polyaxial bone anchors allow for inserting a spherical head of a bone screw into a receiver by pushing the head against a spring force of a resilient member. However, there is still a need for a coupling assembly and a polyaxial bone anchor with such a coupling assembly that is improved with regard to several aspects, such as the efficiency and safety of the coupling.

It is an object of the invention to provide a coupling assembly for coupling a rod to a bone anchoring element, and a polyaxial bone anchor comprising such a coupling assembly, that provides a safe connection of the bone anchoring element to the coupling assembly with a low insertion force, while also providing a high retention force, and where only a small amount of axial travel or displacement is needed to insert the bone anchoring element into the coupling assembly.

The coupling assembly includes a receiving part with an accommodation space for accommodating the head of the bone anchoring element and a retainer element configured to be positioned at least partially in the accommodation space. The retainer element includes at least one spring portion that is compressible in an axial direction and extends in an axial direction up to at least a position that is higher than a bottom of a channel of the receiving part that is configured to receive a rod. The spring portion can generate a sufficient spring force that facilitates a snap-over of the retainer element on the head of the bone anchoring element when the spring portion is biased. The spring portion may be realized by, for example, a snake spring that is small-sized in a radial direction, as seen from a central axis of the receiving part, and that can be, for example, larger in an axial direction.

The retainer element may further have at least one horizontal slit at its bottom end that contributes to a low insertion force requirement for inserting the head into the retainer element. Simultaneously, a retention force that holds the head in the receiving part may be higher compared to the insertion force. Therefore, the bone anchoring element is effectively prevented from being inadvertently pulled-out from a lower opening of the receiving part. In addition, because of a small or reduced insertion path, occurrences of milling under the head or sticking out of the head from bone can be avoided or reduced.

The coupling assembly may further include a pressure element for exerting pressure onto the head of the bone anchoring element to lock the bone anchoring element in a specific angular position relative to the receiving part. The retainer element may encompass at least a portion of the pressure element from an outer side thereof, so that increasing a height of the receiving part for accommodating both the retainer element and the pressure element may not be necessary. Hence, a low profile implant can be provided.

In addition, the receiving part is monolithic and sized such that the retainer element and the pressure element can be mounted from the top opening thereof.

The pressure element may be held in a position such that the head of the bone anchoring element is held by a frictional force exerted by the pressure element onto the head. The frictional force may be such that the head can still be pivoted by applying a force to overcome the frictional force.

The coupling assembly can be assembled in situ with a bone anchoring element that has been already inserted into a bone or a vertebra.

With a coupling assembly according to embodiments of the invention, a modular polyaxial bone anchoring device can be provided that may include several bone anchoring elements that differ with respect to the length of the shank, anchoring features of the shank, such as different thread types and/or thread pitches, different diameters of the shank, and/or with respect to the shank being cannulated or non-cannulated, among other features.

BRIEF DESCRIPTION OF THE DRAWINGS

Further features and advantages of the invention will become more apparent from the description of various embodiments using the accompanying drawings. In the drawings:

FIG. 1 shows a perspective exploded view of a first embodiment of a bone anchoring device.

FIG. 2 shows a perspective view of the bone anchoring device of FIG. 1 in an assembled state.

FIG. 22b shows an enlarged cross-sectional view of a detail of FIG. 22a.

DETAILED DESCRIPTION

Figure 3:
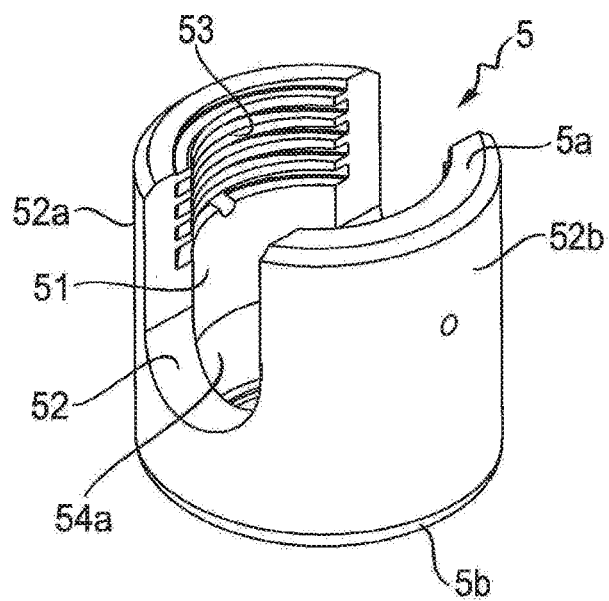
FIG. 3 shows a perspective view from above of a receiving part according to the first embodiment.
Figure 4:
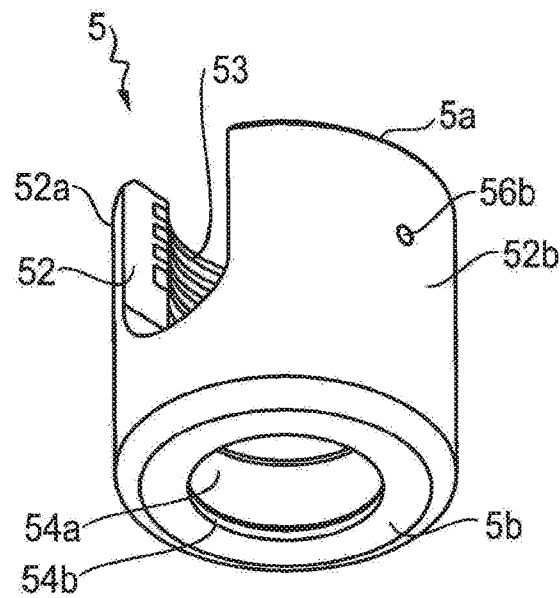
FIG. 4 shows a perspective view from a bottom of the receiving part shown in FIG. 3.
Figure 5:
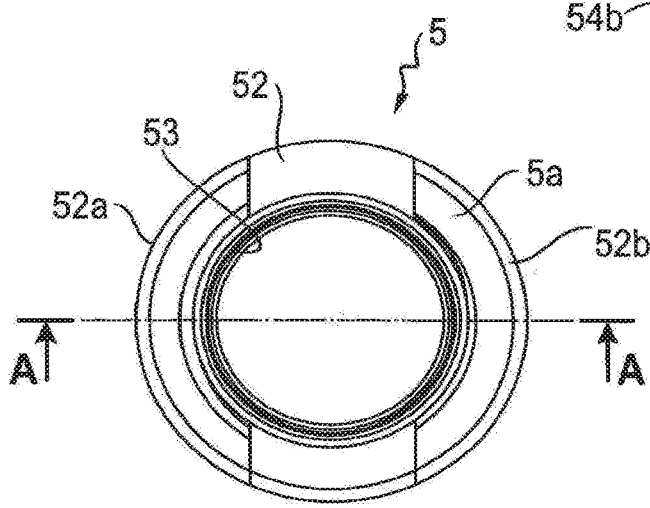
FIG. 5 shows a top view of the receiving part shown in FIGS. 3 and 4.
Figure 6:
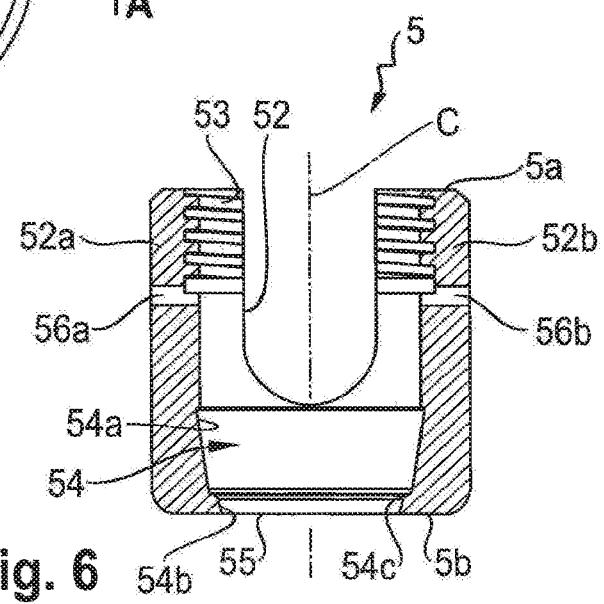
FIG. 6 shows a cross-sectional view of the receiving part shown in FIGS. 3 to 5, the cross-section being taken along line A-A in FIG. 5.
Figure 7:
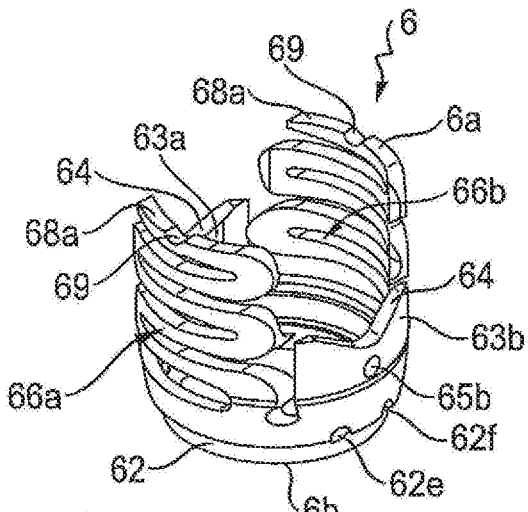
FIG. 7 shows a perspective view from above of a retainer element according to the first embodiment.
Figure 8:
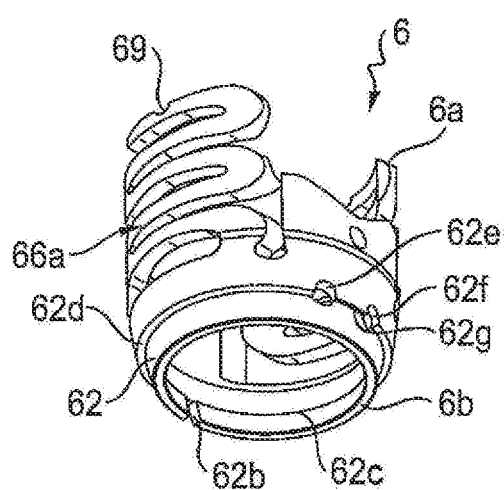
FIG. 8 shows a perspective view from a bottom of the retainer element of FIG. 7.
Figure 9:
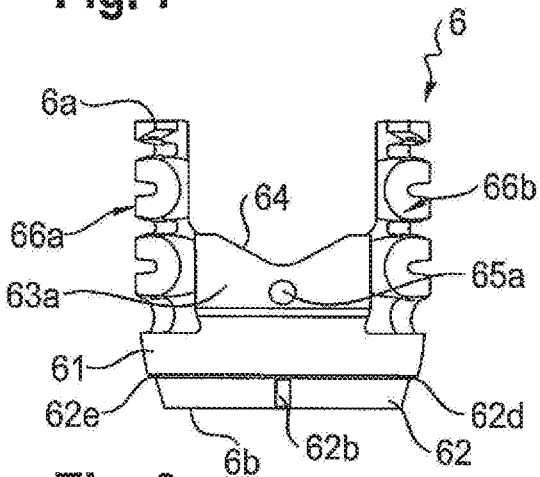
FIG. 9 shows a side view of the retainer element of FIGS. 7 and 8.
Figure 10:
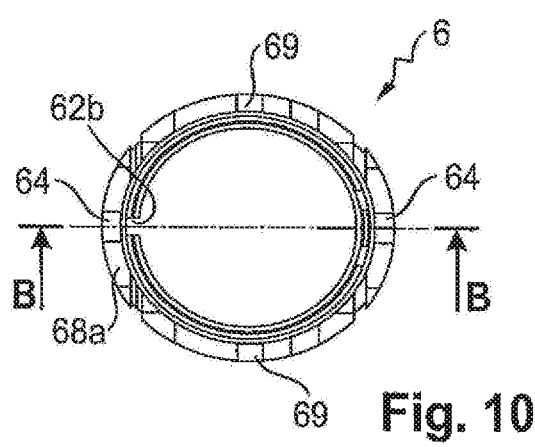
FIG. 10 shows a top view of the retainer element of FIGS. 7 to 9.
Figure 11:
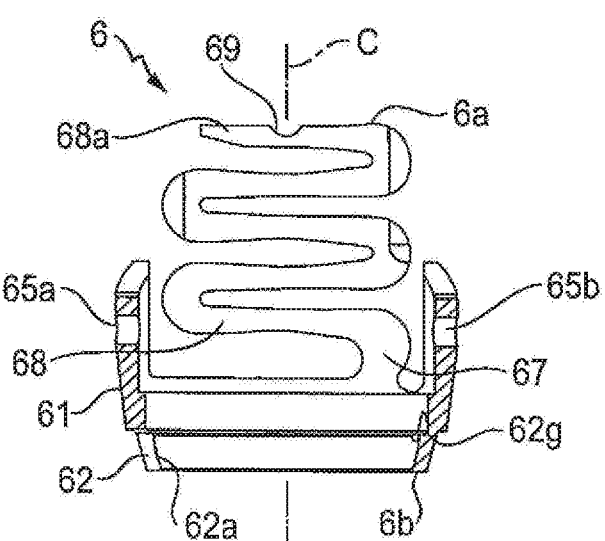
FIG. 11 shows a cross-sectional view of the retainer element of FIGS. 7 to 10, the cross-section being taken along line B-B in FIG. 10.

As shown in FIGS. 1 and 2, a bone anchoring device according to a first embodiment includes a bone anchoring element 1 in the form of a bone screw having a threaded shank 2 and a head 3. The head 3 has a spherical segment-shaped outer surface portion 3a, including a greatest outer diameter E of the sphere, and a free end with a recess 3b for engagement with a screwing-in tool. The bone anchoring device further includes a coupling assembly 4 for coupling a stabilization rod 100 to the bone anchoring element 1. The coupling assembly 4 includes a receiving part 5, and a retainer element 6 and a pressure element 7 configured to be arranged in the receiving part 5. The pressure element 7 serves for locking the head 3 in the receiving part 5. Pins 8a, 8b may also be provided for holding the pressure element 7 in the receiving part 5.

In addition, a locking element 9 in the form of an inner screw is provided for securing the rod 100 in the receiving part 5 and for locking the whole device.

Referring in particular to FIGS. 3 to 6, the receiving part 5 is a monolithic part that has a first end or top end 5a and an opposite second end or bottom end 5b, and a central axis of symmetry C passing through the top end 5a and the bottom end 5b. A bore 51 is provided that is coaxial with the central axis C. In a first region adjacent to the first end 5a, the receiving part 5 has a substantially U-shaped recess 52 with a bottom directed towards the bottom end 5b and two free lateral legs 52a, 52b extending towards the top end 5a. On the legs 52a, 52b, an internal thread 53 is provided that cooperates with the locking element 9. The channel formed by the U-shaped recess 52 is sized so as to receive the rod 100 therein for connecting a plurality of bone anchoring devices. In a region below the legs 52a, 52b, there is an accommodation space 54 configured for receiving the head 3 of the bone anchoring element 1 and for receiving at least partially the retainer element 6 and the pressure element 7. The accommodation space 54 has a first section 54a with a slightly larger upper inner diameter than the inner diameter of the coaxial bore 51, and which tapers and narrows towards the bottom end 5b of the receiving part 5. In this embodiment, the section 54a has a hollow cone shape, however, other shapes may also be contemplated. The accommodation space 54 further has a second portion 54b that conically tapers towards the bottom end 5b. The second portion 54b forms a seat for a portion of the retainer element 6. Between the two portions 54a, 54b, a shoulder 54c is provided that projects inward and serves as a stop for another portion of the retainer element 6, as described in greater detail below.

The accommodation space 54 further has an opening 55 at the bottom end 5b, the inner diameter of which is larger than the greatest outer diameter E of the head 3 of the bone anchoring element 1, so that the head 3 can be inserted into the receiving part 5 from the bottom end 5b. The legs 52a, 52b each includes a through-hole in the form of a transverse pin hole 56a, 56b that is located substantially centrally in the legs 52a, 52b, and that serves for receiving the pins 8a, 8b. The pins 8a, 8b have a length such that once a pin 8a, 8b is inserted into a respective pin hole 56a, 56b, the pin 8a, 8b extends a short distance into the bore 51 to provide a stop for securing a rotational position of the pressure element 7. Furthermore, the pins 8a, 8b also have a function of providing an abutment for a spring portion of the retainer element 6. The pins 8a, 8b may be flush with an outer surface of the receiving part 5 when inserted in the pin holes 56a, 56b.

Referring in more detail to FIGS. 7 to 11, the retainer element 6 will be explained. The retainer element 6 is a substantially sleeve-like part, with a first end or top end 6a and an opposite second end or bottom end 6b. The retainer element 6 is hollow between the top end 6a and the bottom end 6b. The retainer element includes a first portion 61 in the form of a closed ring that has an outer conical surface tapering and narrowing towards the bottom end 6b and an inner hollow cylindrical surface. The first portion 61 is sized so that the first portion 61 fits into the lower portion of the first section 54a of the accommodation space 54 and abuts against the conical inner surface of the first section 54a. An inner diameter of the inner cylindrical surface of the first portion 61 is greater than the largest outer diameter E of the head 3.

Between the first portion 61 and the bottom end 6b, the retainer element 6 has the form of a slit ring 62. The slit ring 62 has a substantially conical outer surface that matches the inner surface of the second section 54b of the accommodation space 54. An inner surface 62a of the slit ring 62 has the shape of a hollow spherical segment that matches the spherical shape of the head 3 so that the slit ring 62 provides a seat for the head 3, to form a ball and socket joint between the receiving part 5 and the bone anchoring element 1. The slit ring 62 is formed by a first vertical slit 62b extending from the bottom end 6b in a substantially vertical direction. From the vertical slit 62b two opposite horizontal slits 62c, 62d extend circumferentially around the central axis C. The horizontal slits 62c, 62d end in widened end portions 62e, 62f. The portion between the end portions 62e, 62f forms a connecting portion 62g that connects the slit ring 62 to the first portion 61 of the retainer element 6. Hence, the slit ring 62 is integrally connected to the rest of the retainer element 6. By means of the slits 62b, 62c, 62d, the slit ring 62 is configured to be expanded and compressed in a radial direction. The widths of the vertical slit 62b and of the horizontal slits 62c, 62d as well as the width of the connecting portion 62g, may be selected such that a desired flexibility of the slit ring 62 is obtained.

From the first portion 61, two upstanding rod supporting projections 63a, 63b that are offset from each other by 180° extend towards the top end 6a. The upstanding projections 63a, 63b each has an outer and an inner cylindrical surface portion, and a groove 64 provided at its free end that may be substantially V-shaped and sized so as to receive rods of different diameters. The rod supporting projections 63a, 63b extend up to a height, such that a bottom of the V-shaped groove 64 is positioned slightly above the bottom of the U-shaped recess 52 of the receiving part 5 when the retainer element 6 is seated in the receiving part 5. Beneath the bottom of the V-shaped groove 64, a transverse pin hole 65a, 65b is respectively provided at each of the rod supporting projections 63a, 63b. The pin holes 65a, 65b extend fully through the rod supporting projections 63a, 63b and serve for receiving a pin for coupling the retainer element 6 to the pressure element 7, as explained in greater detail below.

Between the rod supporting projections 63a, 63b, there are two spring portions 66a, 66b, that are respectively provided on either side of the V-shaped groove 64 and that project in an axial direction over the rod supporting projections 63a, 63b, such that the top end 6a of the retainer element 6 is formed by the end surfaces of the spring portions 66a, 66b. The spring portions 66a, 66b each have an outer cylindrical surface with an outer diameter that is only slightly smaller than an inner diameter of the bore 51 of the receiving part 5 so that, as can be seen for example in FIG. 26, the spring portions 66a, 66b fit into the bore 51. The spring portions 66a, 66b further have an inner cylindrical surface that is configured to fit around an outer cylindrical surface of the pressure element 7, as can also be seen in FIG. 26. The design of the spring portions 66a, 66b resembles that of a snake spring. Each spring portion 66a, 66b has alternating substantially vertical sections 67 and horizontal sections 68, wherein the horizontal sections 68 are preferably longer than the vertical sections 67, and wherein the vertical sections 67 and the horizontal sections 68 form a meandering structure, meandering around a central axis c that extends parallel to the central axis C of the receiving part 5 when the retainer element 6 is seated in the receiving part 5.

By means of this, the retainer element 6 is compressible in a vertical direction when pressure is exerted onto the spring portions 66a, 66b, such that a height of the spring portions 66a, 66b change from a first height to a second height that is smaller than the first height. An uppermost horizontal section 68a of each of the spring portions 66a, 66b has a free end and may further have a cylinder segment-shaped recess 69 for receiving the pins 8a, 8b. It shall be noted that the lengths of the vertical sections 67 and the horizontal sections 68, and other parameters of the spring portions 66a, 66b, may be selected such that a desired resiliency is achieved. Also, the vertical sections 67 and the horizontal sections 68 need not be exactly vertical or horizontal, but may instead be inclined. The spring portions 66a, 66b may be easily manufactured by cutting a cylindrical tube. A height of the retainer element 6 is such that when the retainer element 6 is seated in the receiving part 5 with the slit ring 62 arranged in the second portion 54b of the accommodation space 54, the uppermost horizontal sections 68a of the spring portions 66a, 66b abut against the pins 8a, 8b provided in the receiving part 5.

Referring in greater detail to FIGS. 12 to 15, the pressure element 7 is a substantially cylindrical part, with a first end or top end 7a and an opposite second end or bottom end 7b. Adjacent to the bottom end 7b, there is a substantially spherical segment-shaped recess 71 that matches the spherical surface of the head 3 and provides a head contacting surface portion. Adjacent to the top end 7a, a rod receiving channel 72 is provided that has two substantially flat and parallel side walls 72a, 72b and a substantially V-shaped bottom 72c. The size of the channel is such that a distance between the side walls 72a, 72b is only slightly larger than a diameter of a largest rod to be received therein. The pressure element 7 further has a coaxial bore 73 that allows access to the recess 3b in the head 3 of the bone anchoring element 1 with a tool.

Figure 12:
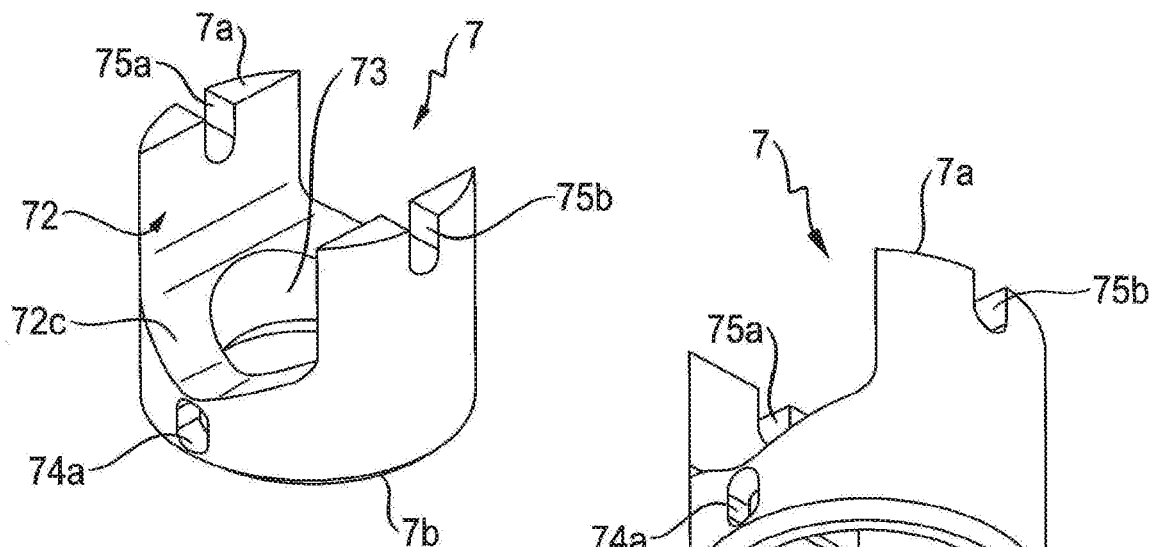
FIG. 12 shows a perspective view from above of a pressure element according to the first embodiment.
Figure 13:
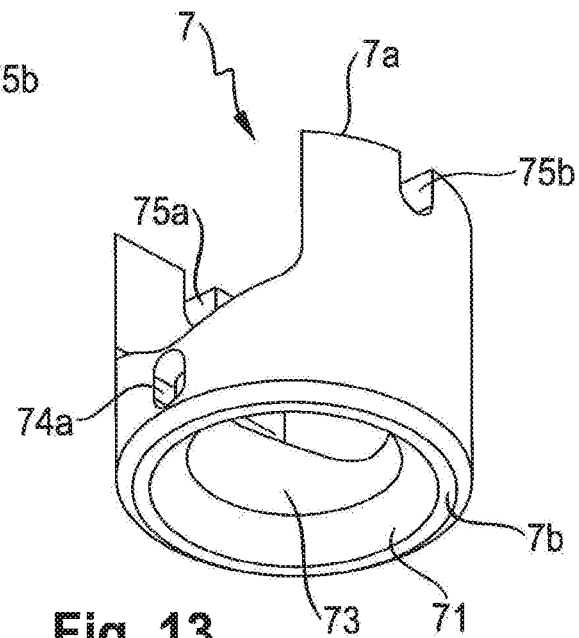
FIG. 13 shows a perspective view from a bottom of the pressure element of FIG. 12.
Figure 14:
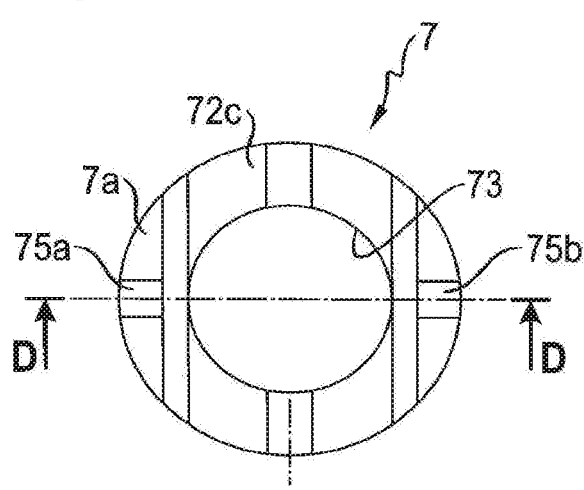
FIG. 14 shows a top view of the pressure element of FIGS. 12 and 13.
Figure 15:
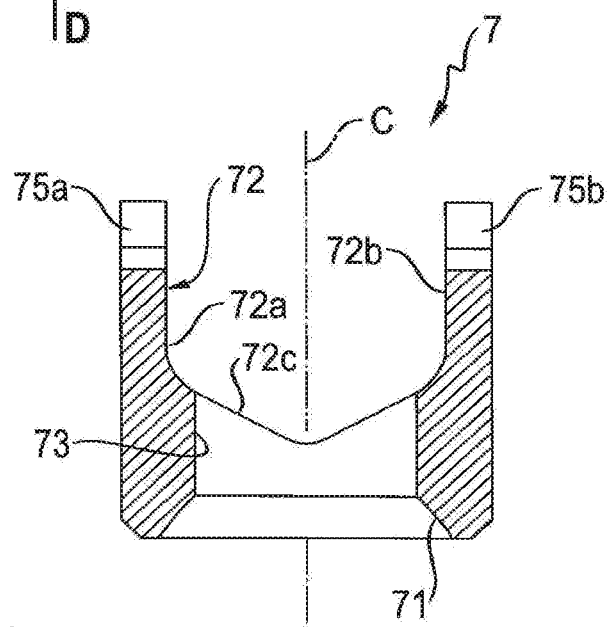
FIG. 15 shows a cross-sectional view of the pressure element of FIGS. 12 to 14, the cross-section being taken along line D-D in FIG. 14.

As can be seen in particular in FIGS. 12 and 13, at either side of the V-shaped bottom of the channel 72, an elongate hole 74a, 74b (only one of which is shown in the Figures) extends in an axial direction. The elongate holes 74a, 74b are configured to receive pins 10a, 10b (see FIG. 17) for coupling the retainer element 6 and the pressure element 7 together. The pins 10a, 10b can move in the elongate holes 74a, 74b in an axial direction, where the movement is limited by the upper and lower ends of the elongate holes 74a, 74b. At each side wall 72a, 72b, a U-shaped recess 75a, 75b extends from the top end 7a to a distance therefrom. The U-shaped recesses 75a, 75b are open to the top end 7a and are configured to be engaged by the pins 8a, 8b. The bottoms of the recesses 75a, 75b provide stops for the pins 8a, 8b, respectively.

The bone anchoring device, as a whole or in part, may be made of a bio-compatible material, such as a bio-compatible metal or a metal alloy, for example titanium, stainless steel, a nickel titanium alloy, for example Nitinol, or of one or more bio-compatible plastic materials, such as, for example polyether ether ketone (PEEK), or of a bio-compatible ceramic material.

Figure 16:
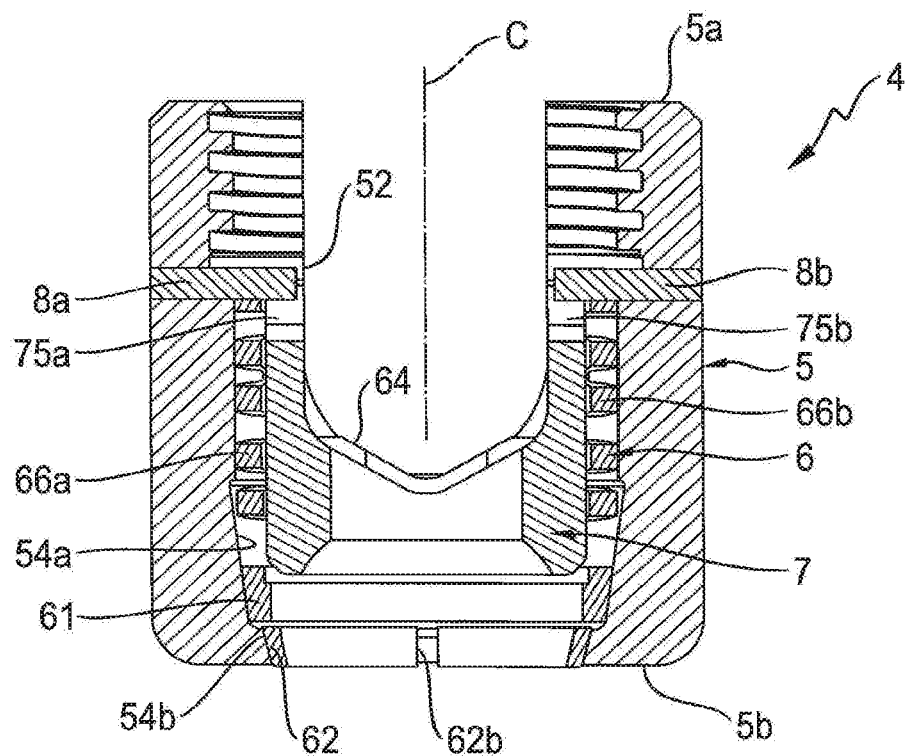
FIG. 16 shows a cross-sectional view of a coupling assembly according to the first embodiment in an assembled state, the cross-section being taken in a plane perpendicular to an axis of a rod to be inserted in the coupling assembly.
Figure 17:
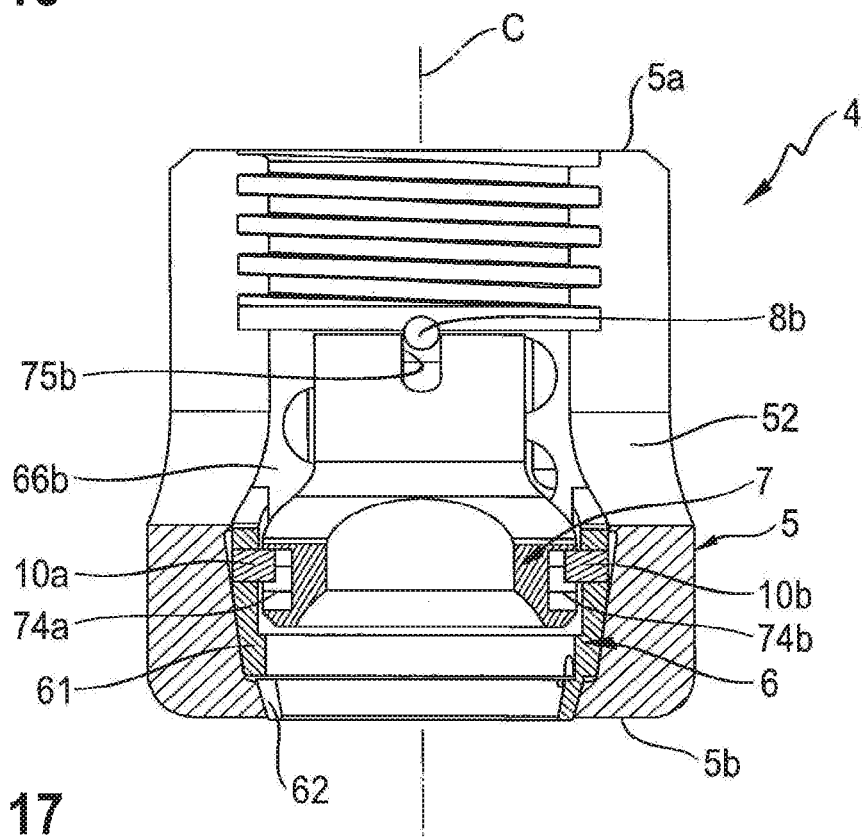
FIG. 17 shows a cross-sectional view of the coupling assembly of FIG. 16, rotated by 90°.

The pressure element 7 and the retainer element 6 may be pre-assembled in such a manner that, as can be seen in particular in FIGS. 16 and 17, the pressure element 7 extends into the retainer element 6, such that the V-shaped groove 64 of the retainer element 6 is aligned with the channel 72 of the pressure element 7. The pins 10a, 10b are inserted into the pin holes 65a, 65b of the retainer element 6 and extend into the elongate holes 74a, 74b of the pressure element 7. The pins 10a, 10b are mounted in a substantially press-fit manner in the holes 65a, 65b. By means of this, the retainer element 6 and the pressure element 7 are movable relative to each other in an axial manner, whereby the movement is limited by the abutment of the pins 10a, 10b at the upper and lower ends of the elongate holes 74a, 74b of the pressure element 7.

The pre-assembled retainer element 6 and pressure element 7 are inserted into the receiving part 5 from the top end 5a through the coaxial bore 51, so that the slit ring 62 is seated in the second portion 54b of the accommodation space 54, as can be seen in FIGS. 16 and 17. As further depicted in FIGS. 16 and 17, after the pre-assembled retainer element 6 and pressure element 7 have been inserted into the receiving part 5, the two pins 8a, 8b are inserted into the pin holes 56a, 56b of the receiving part 5 until their front ends project into the coaxial bore 51. A first function of the pins 8a, 8b is to provide a stop for the spring portions 66a, 66b of the retainer element 6. A second function of the pins 8a, 8b is to limit the path of movement of the pressure element 7 in the direction towards the top end 5a of the receiving part 5. A third function of the pins 8a, 8b is to secure the pressure element 7 and the retainer element 6 against rotation in the receiving part 5.

As shown in particular in FIG. 17, during assembly of the retainer element 6 with the pre-assembled pressure element 7, the pins 8a, 8b are located at the upper end of the U-shaped recesses 75a, 75b. The retainer element 6 is pressed down by the two spring portions 66a, 66b. The pressure element 7 rests with the upper end of the elongated holes 74a, 74b on the pins 10a, 10b, respectively, and is still movable with respect to the retainer element 6.

The slit ring 62 is seated in the conical second portion 54b of the accommodation space 54, and the pins 8a, 8b hold the spring portions 66a, 66b. When the slit ring 62 is positioned in the seat 54b, the lower edge 6b of the retainer element 6 projects slightly out of the lower opening 55 receiving part 5.

Figure 18:
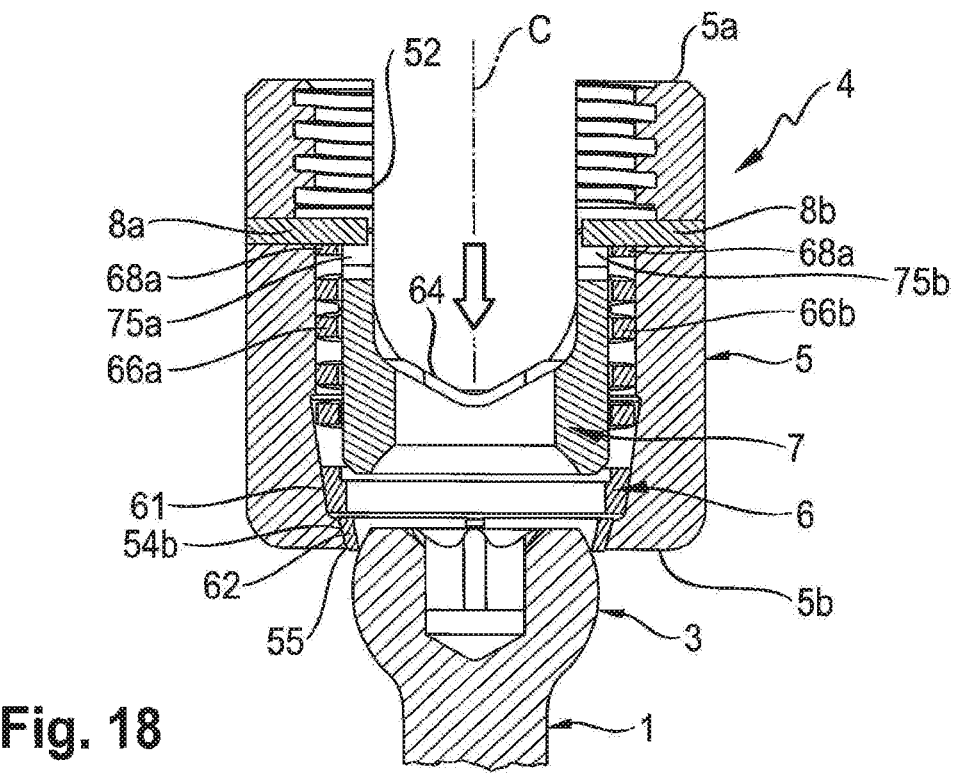
FIGS. 18 and 19 show cross-sectional views in planes perpendicular to the rod axis and rotated by 90°, respectively, of the coupling assembly during first step of mounting or inserting the bone anchoring element.
Figure 19:
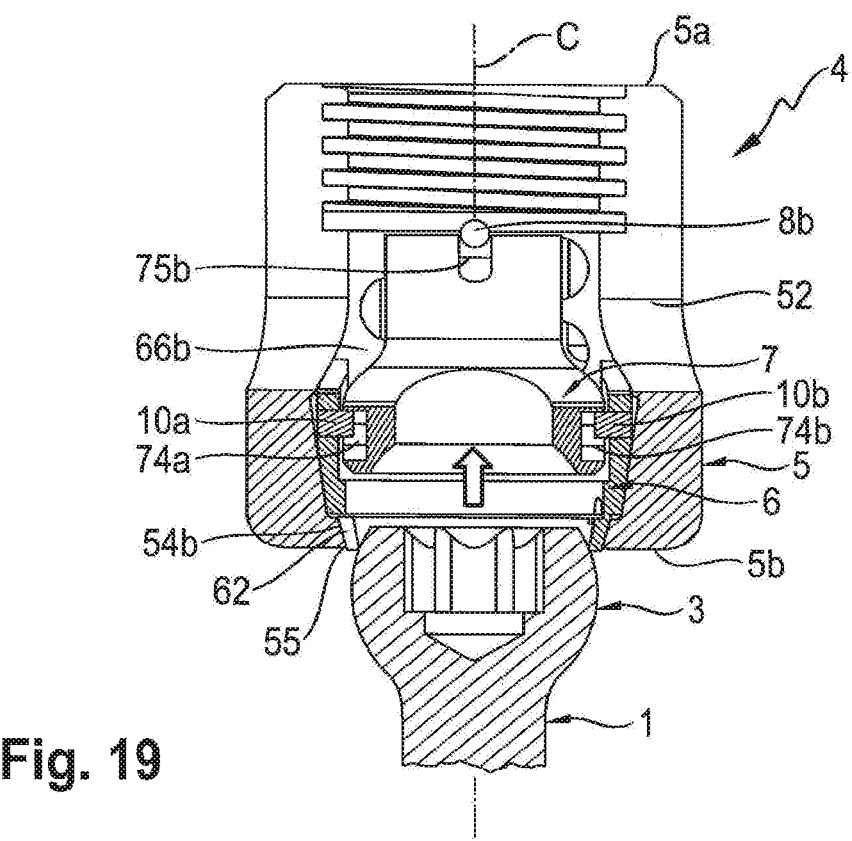

Next, as depicted in FIGS. 18 and 19, the head 3 of the bone anchoring element 1 is inserted into the receiving part 5 through the lower opening 55. The head 3 may first begin entering the lower portion of the slit ring 62 that projects slightly through or out of the lower opening 55.

Figure 20:
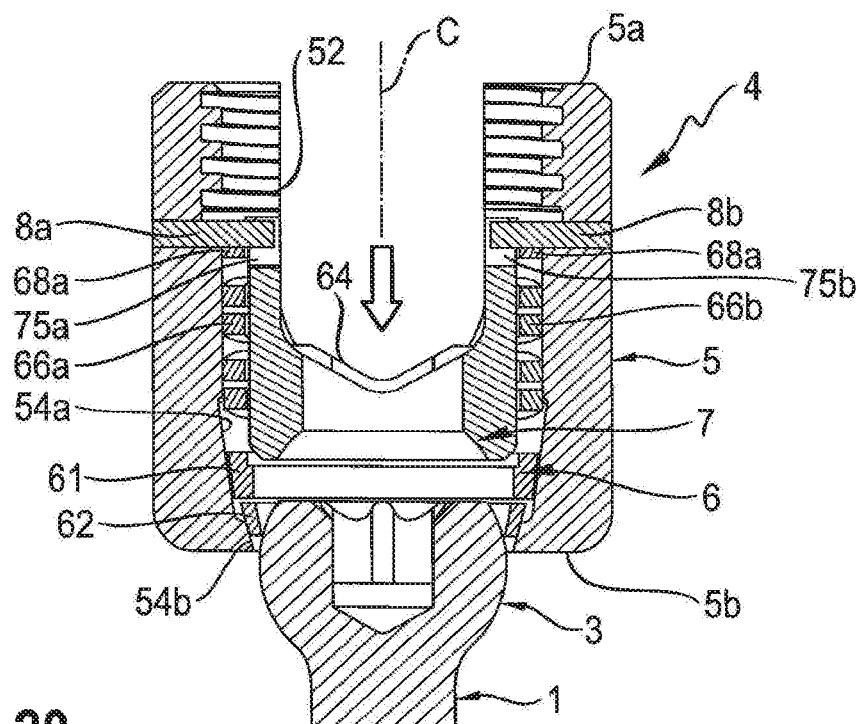
FIGS. 20 and 21 show cross-sectional views in planes perpendicular to the rod axis and rotated by 90°, respectively, of a second step of inserting the bone anchoring element into the coupling assembly.
Figure 21:
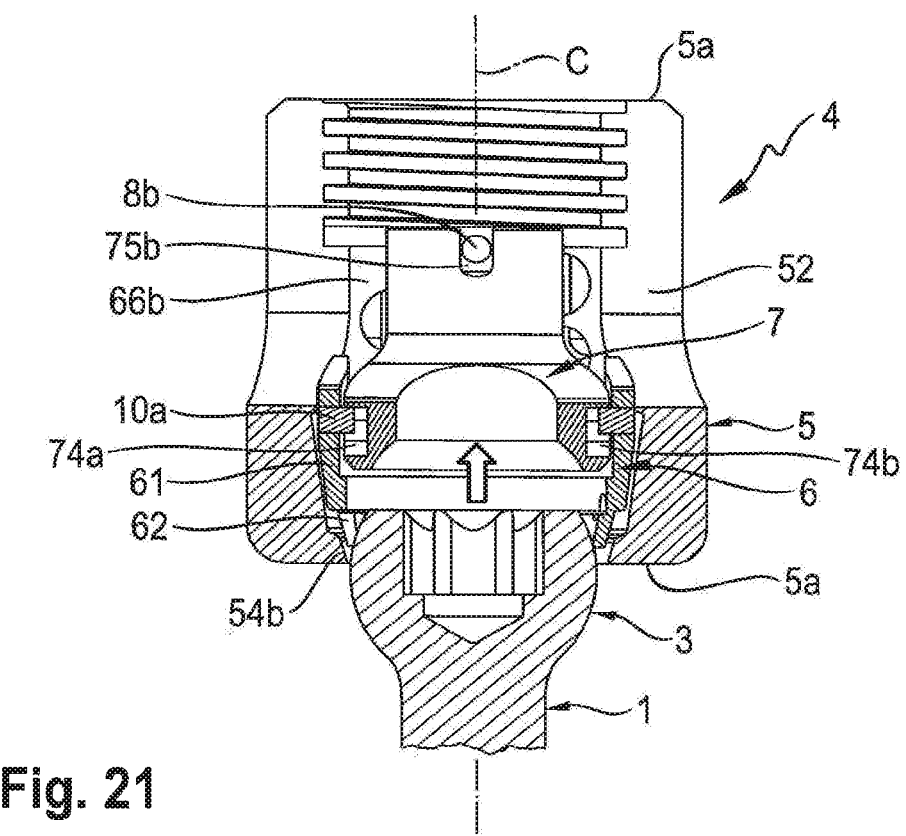

The slit ring 62 is pushed upwards out of its seat 54b by the head 3, as further depicted in FIGS. 20 and 21. The assembly of the retainer element 6 and the pressure element 7 is moved upward towards the top end 5a of the receiving part 5, whereby the pins 8a, 8b enter deeper into the V-shaped recesses 75a, 75b of the pressure element 7. During the upward movement, the spring portions 66a, 66b are compressed, because their upper ends 68a with the recesses 69 abut against the pins 8a, 8b. In addition, the slit ring 62 is expanded when the head 3 enters further into it. Because the retainer element 6 and the pressure element 7 are coupled together via the pins 10a, 10b, the pressure element 7 may also be moved upwards.

Figure 22A:
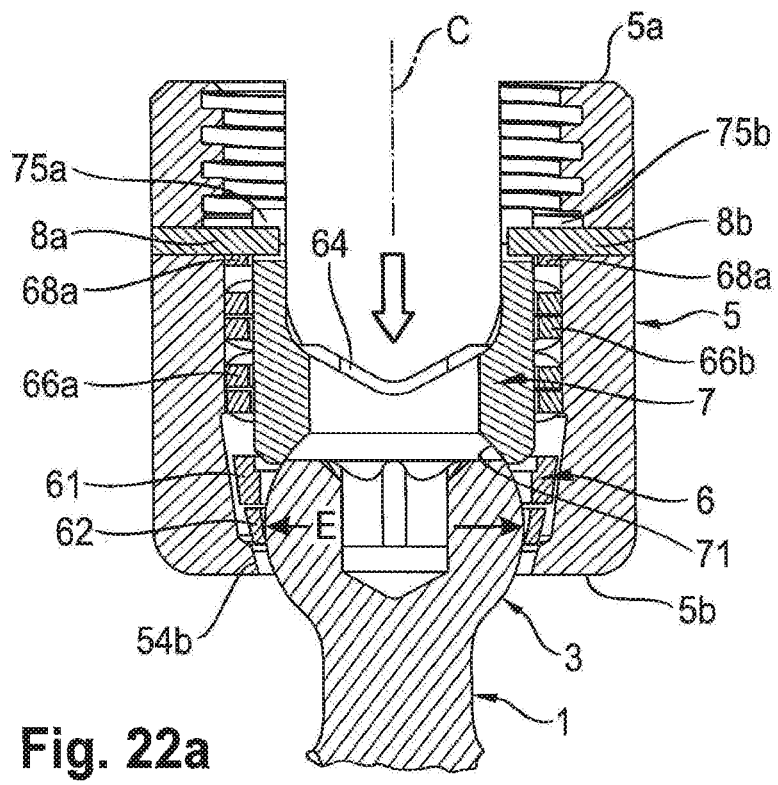
FIG. 22a shows a cross-sectional view in a plane perpendicular to the rod axis of a third step of inserting the bone anchoring element into the coupling assembly.
Figure 22B:
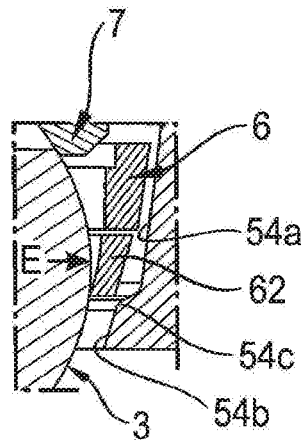
Figure 23:
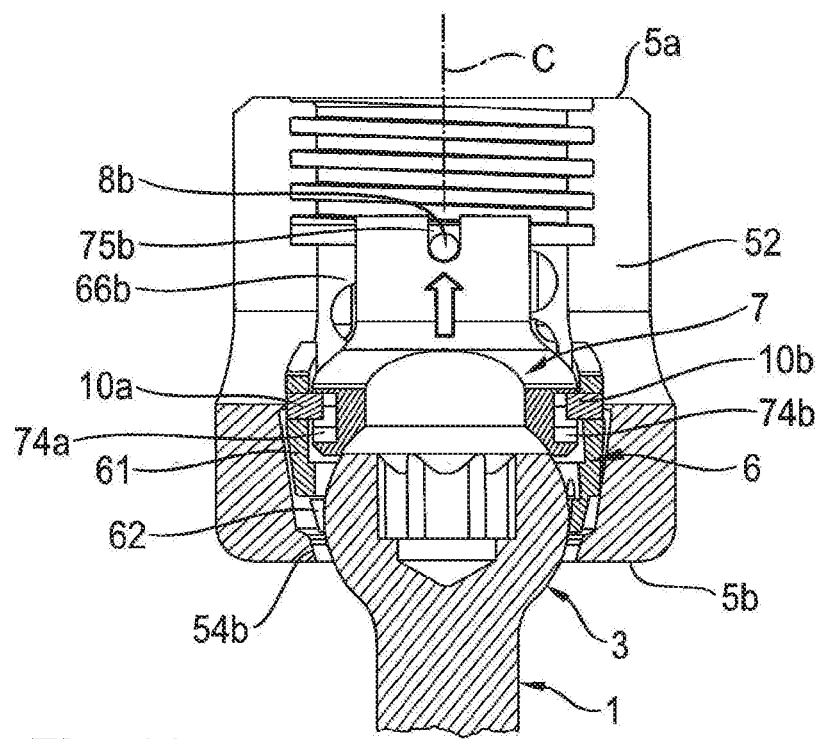
FIG. 23 shows a cross-sectional view of the coupling assembly of FIG. 22a, the plane of the cross-section being rotated by 90° from FIG. 22a, i.e., in a plane containing the rod axis.

Referring further to FIGS. 22a to 23, further insertion of the head 3 causes further expansion of the slit ring 62 and further compression of the spring portions 66a, 66b. When a counterforce exerted by the compressed spring portions 66a, 66b is greater than a force needed for expanding the slit ring 62 and for sliding the slit ring 62 over the portion of the head 3 having the largest diameter E, the spring force of the compressed spring portions 66a, 66b causes the slit ring 62 to snap over the head 3 so that the lower edge 6b of the retainer element 6 slides over the region of the head 3 with the largest diameter E (see FIG. 22b). The head 3 can be inserted into the coupling assembly 4 only to such an extent that the head 3 abuts against the spherical recess 71 of the pressure element 7. The bottoms of the U-shaped recesses 75a, 75b of the pressure element 7 serve as abutments for the pins 8a, 8b, so that the pressure element 7 and the retainer element 6 cannot escape through the top end 5a of the receiving part 5.

Figure 24:
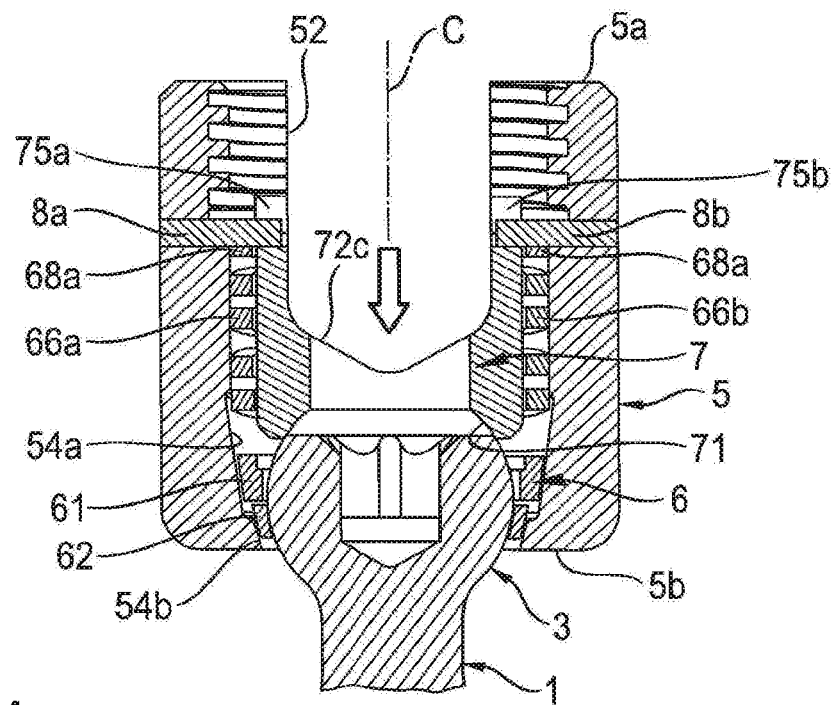
FIGS. 24 and 25 show cross-sectional views in planes perpendicular to the rod axis and rotated by 90°, respectively, of a fourth step of inserting the bone anchoring element into the coupling assembly.
Figure 25:
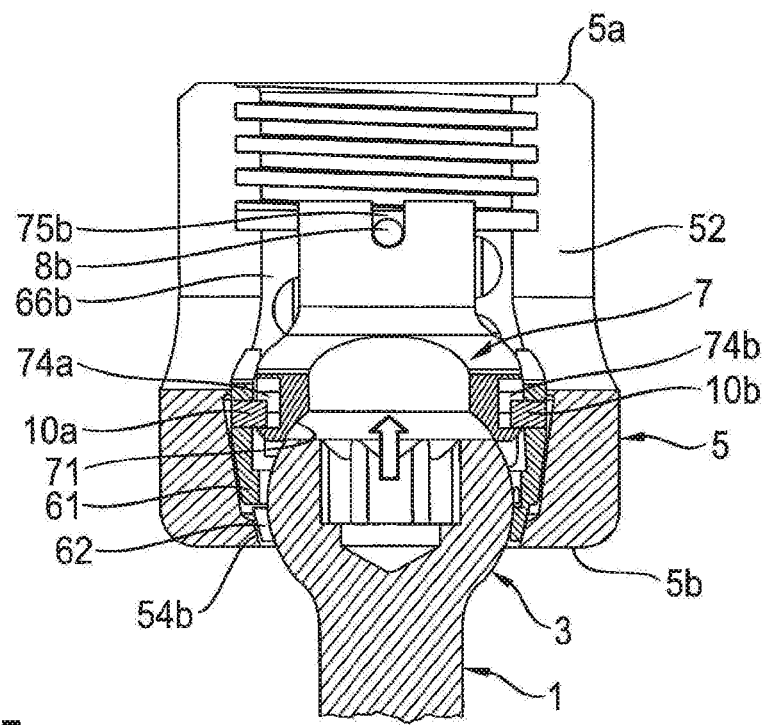

As shown in FIGS. 24 and 25, after the head 3 is fully inserted in the coupling assembly 4, where the pins 8a, 8b abut against the bottom of the U-shaped recesses 75a, 75b, the spring portions 66a, 66b of the retainer element 6 may expand, thereby moving the pins 10a, 10b downward until they abut against the bottom of the elongate holes 74a, 74b of the pressure element 7. The slit ring 62 is positioned below the portion of the head 3 with the largest diameter E. The sliding of the retainer element 6 over the head 3 is supported or facilitated by the spring portions 66a, 66b, and is therefore quick and safe. When the slit ring 62 is below the portion of the head 3 with the greatest diameter E, the head 3 can no longer be pulled-out through the lower openings of either the receiving part 5 or the retainer element 6.

Figure 26:
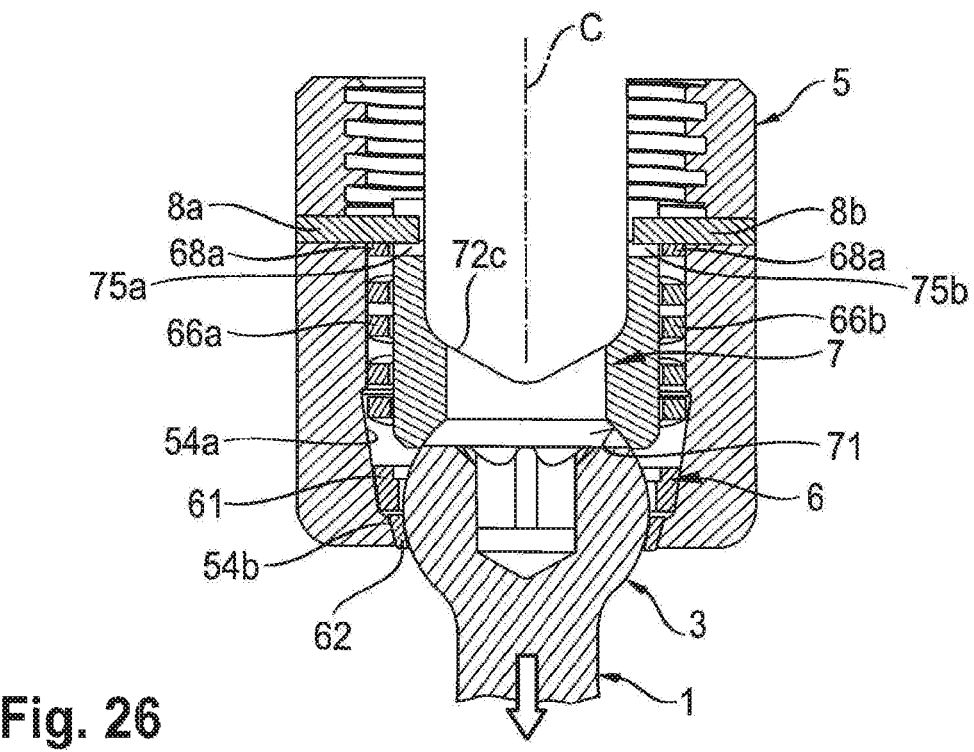
FIGS. 26 and 27 show a cross-sectional view in planes perpendicular to the rod axis and rotated by 90°, respectively, of a final step of assembling the coupling assembly and the bone anchoring element.
Figure 27:
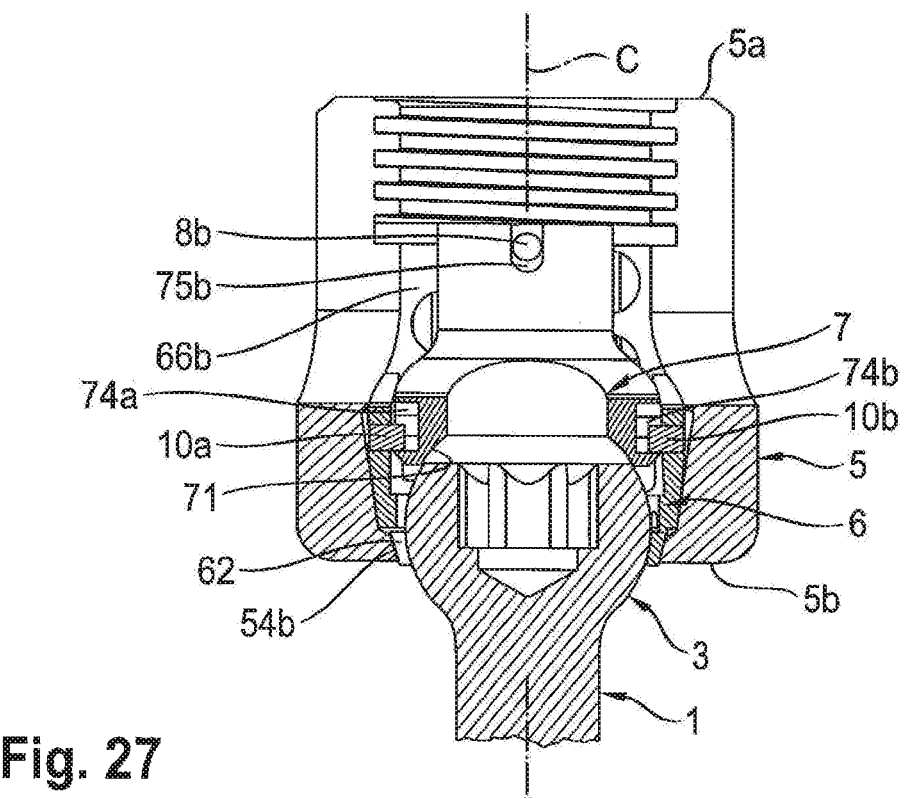

As further shown in FIGS. 26 and 27, when the receiving part 5 is pulled upward or the pressure element 7 is pressed downward, the head 3 presses or urges the slit ring 62 into the seat 54b. This condition is a pre-locking condition, wherein the head 3 is connected to the coupling assembly 4, such that the head 3 cannot be separated from the coupling assembly 4 without applying or utilizing a special instrument.

The inner portion of the slit ring 62 may have a slight undersize with respect to the size of the head 3, such that the slit ring 62 exerts a frictional force on the head 3 when the slit ring 62 is around the head 3. Hence, in the condition shown in FIGS. 26 and 27, the head 3 is held by friction within the receiving part 5, and therefore, the receiving part 5 can be maintained at a specific angular position with respect to the bone anchoring element 1 before locking of the bone anchoring element 1 relative to the receiving part 5. Also the spring force exerted by the spring portions 66a, 66b may further contribute to the friction hold of the head 3 in the receiving part 5 by urging the slit ring 62 into the seat 54b.

Figure 28:
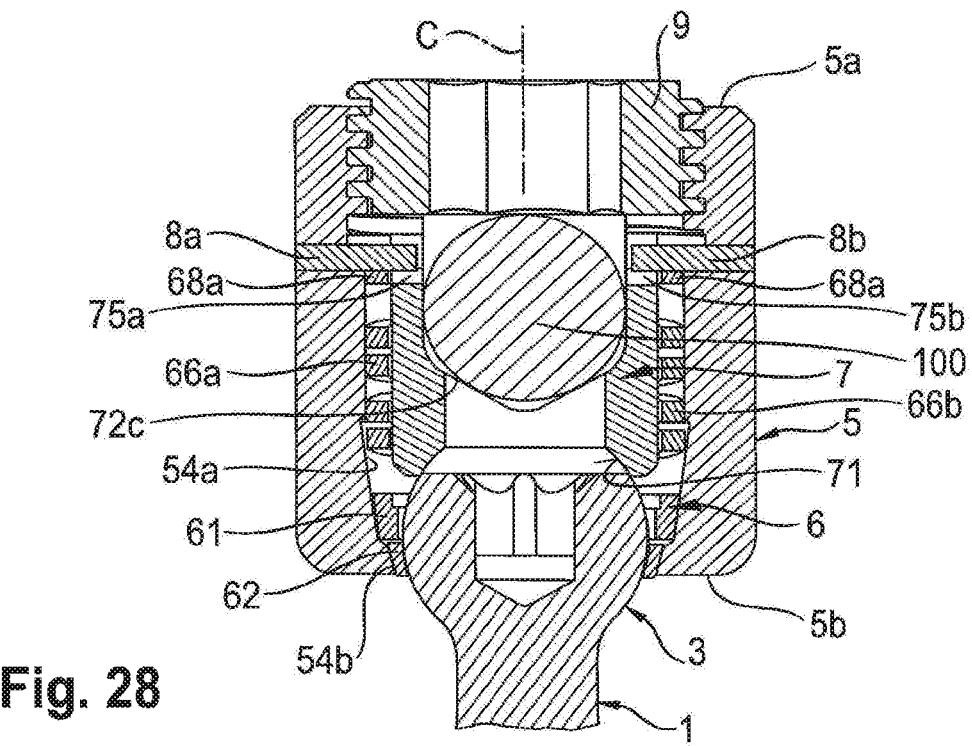
FIGS. 28 and 29 show cross-sectional views of the fully assembled polyaxial bone anchoring device according to the first embodiment, with inserted rod and locking element, in a plane perpendicular to the rod axis and in a plane rotated by 90°, respectively.
Figure 29:
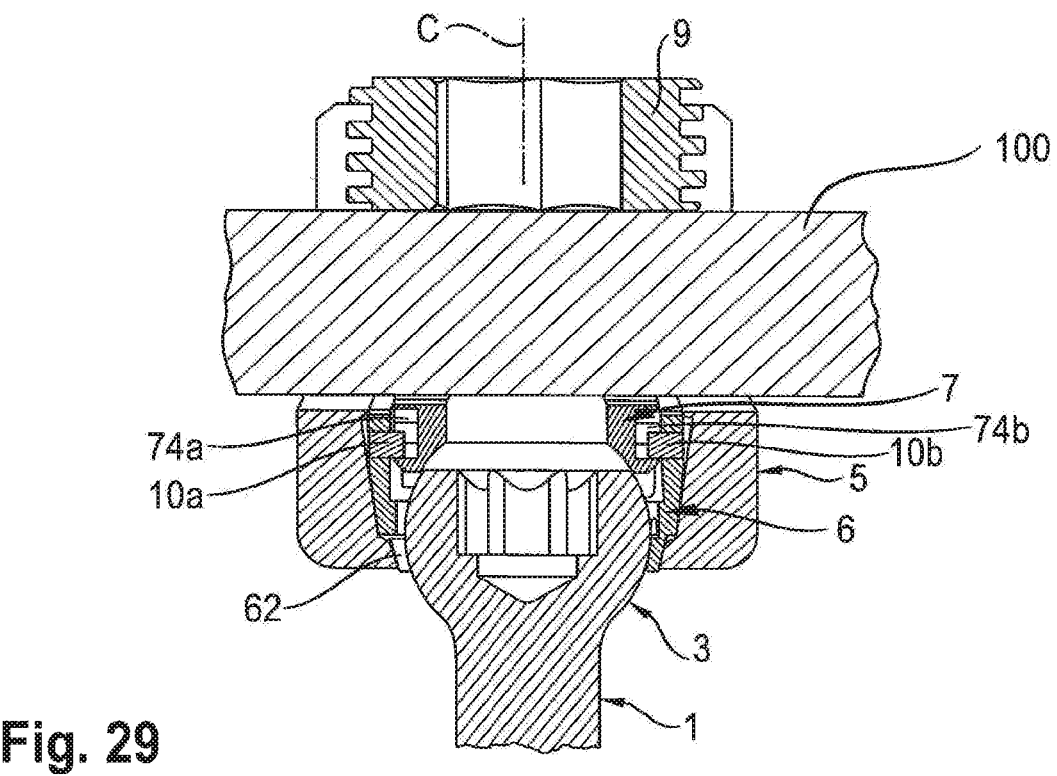

When the rod 100 is mounted in the receiving part 5 and moved downward with the locking element 9, the pressure element 7 presses against the head 3, and the head 3 presses against the slit ring 62. Final tightening of the locking element 9 locks the whole device. The fully locked condition is shown in FIGS. 28 and 29.

In use, the bone anchoring element 1 may be inserted into a bone or into a vertebra prior to mounting the coupling assembly 4. In an alternative manner of use, the bone anchoring element 1 and the coupling assembly 4 are pre-assembled and thereafter can be inserted into the bone or vertebra. A plurality of bone anchoring devices can be connected through the stabilization rod 100.

It shall be noted that while two pairs of pins 8a, 8b and 10a, 10b are shown, the basic functions of the pins may be achieved also with only one pin for coupling the retainer element 6 and the receiving part 7 together and only one pin for forming an abutment for the spring portions 66a, 66b and for holding the pressure element 7 and the retainer element 6 in the receiving part 5.

Figure 30:
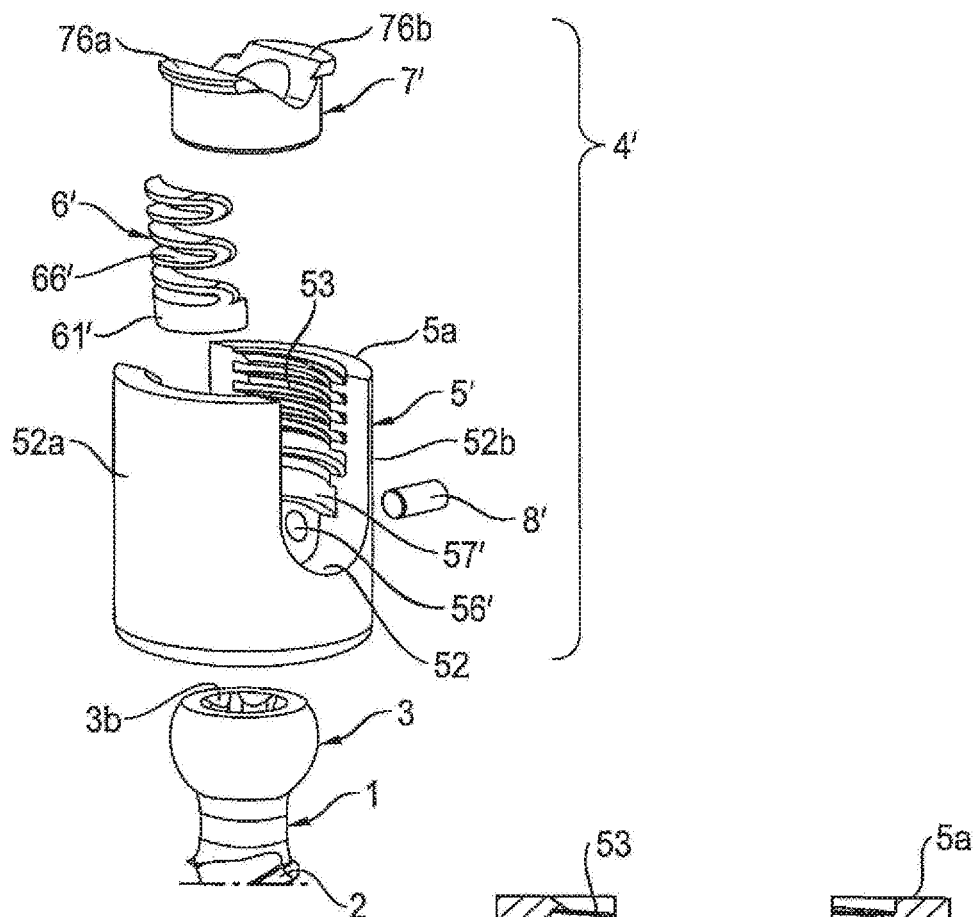
FIG. 30 shows a perspective exploded view of a polyaxial bone anchoring device according to a second embodiment.
Figure 31:
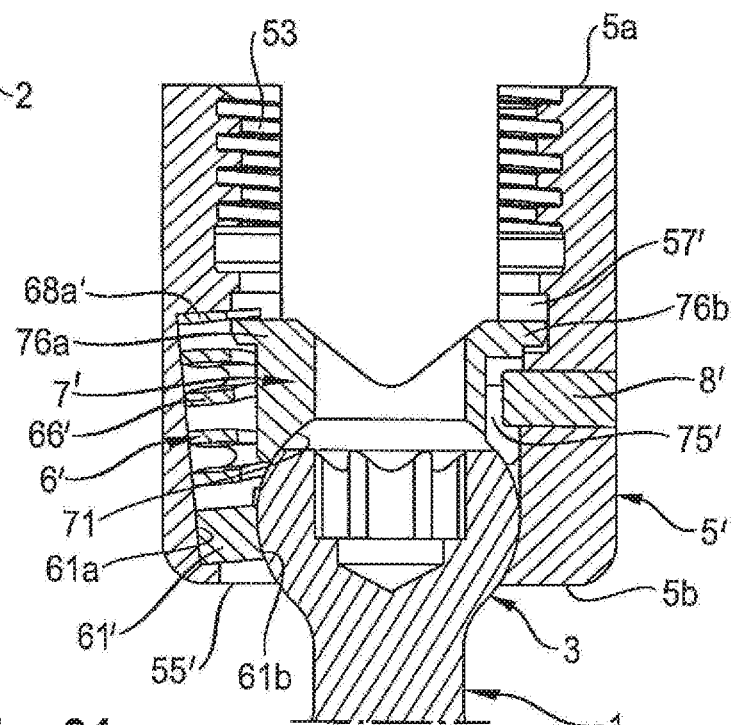
FIG. 31 shows a cross-sectional view of the polyaxial bone anchoring device of FIG. 30 in an assembled state, the cross-section being taken in a plane perpendicular to an axis of an inserted rod.
Figure 32:
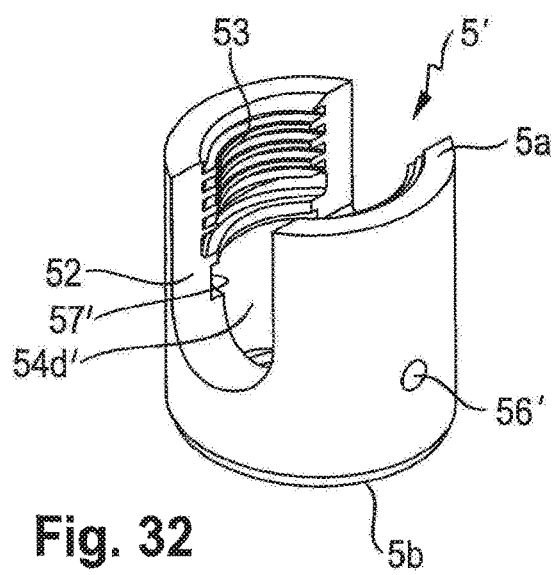
FIG. 32 shows a perspective view from above of a receiving part of the polyaxial bone anchoring device according to the second embodiment.
Figure 33:
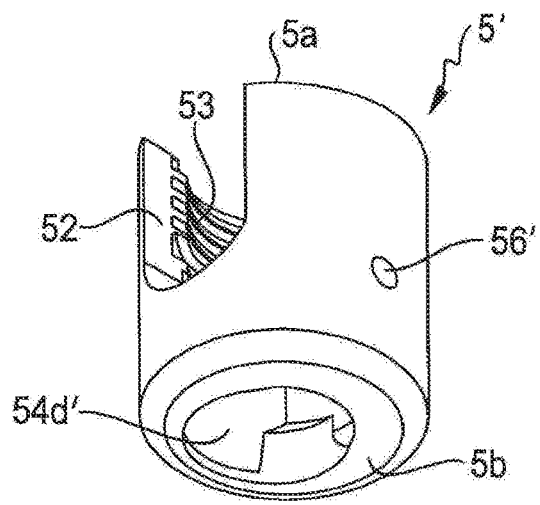
FIG. 33 shows a perspective view from a bottom of the receiving part of FIG. 32.
Figure 34:
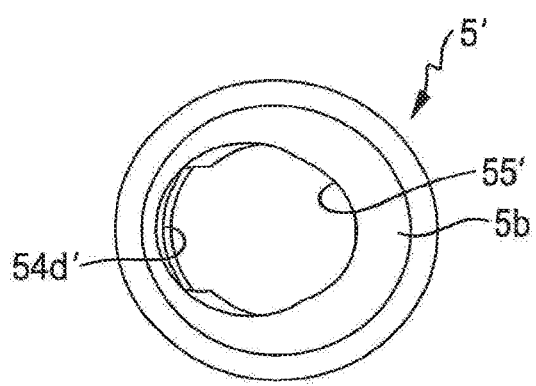
FIG. 34 shows a bottom view of the receiving part of FIGS. 32 and 33.
Figure 36:
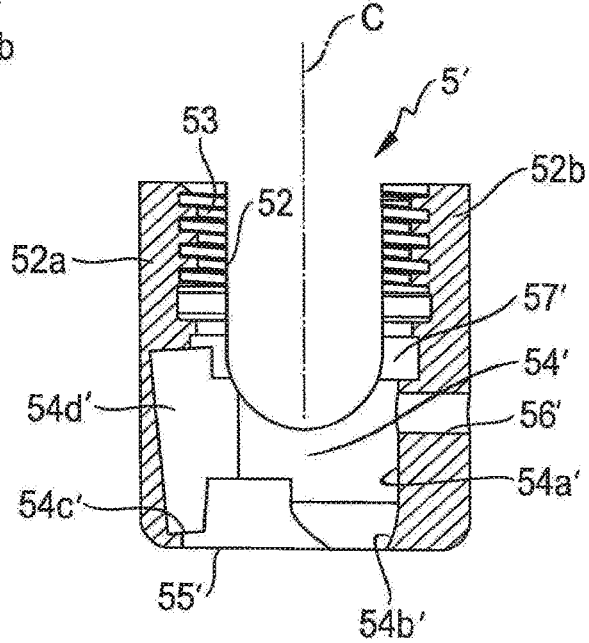
FIG. 36 shows a cross-sectional view of the receiving part of FIGS. 32 to 35, the cross-section being taken along line F-F in FIG. 35.
Figure 35:
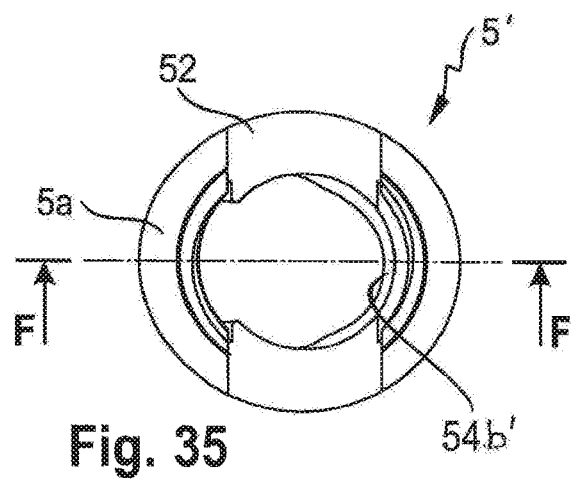
FIG. 35 shows a top view of the receiving part of FIGS. 32 to 34.
Figure 37:
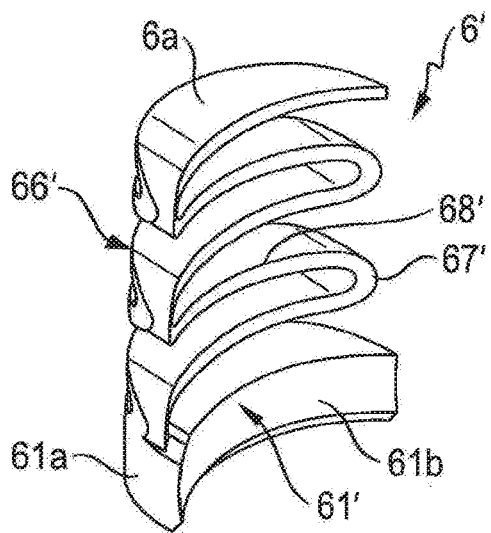
FIG. 37 shows a perspective view of a retainer element of the polyaxial bone anchoring device according to the second embodiment.
Figure 38:
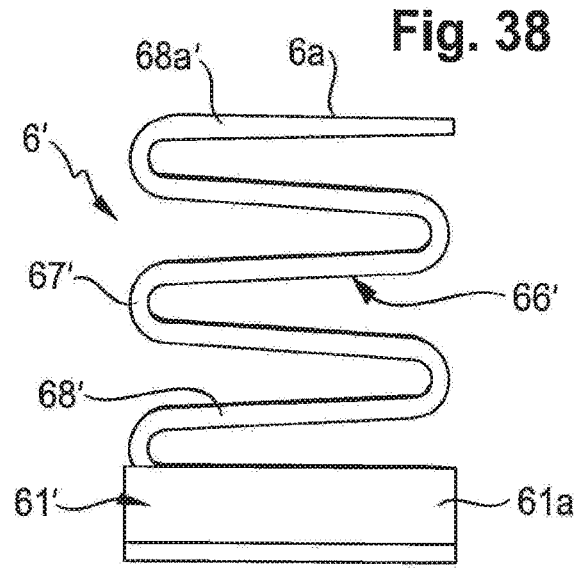
FIG. 38 shows a side view of the retainer element of FIG. 37.

Referring to FIGS. 30 and 31, a second embodiment of the polyaxial bone anchoring device will be described. The polyaxial bone anchoring device according to the second embodiment differs from the polyaxial bone anchoring device according to the first embodiment in the design of the coupling assembly. All parts that are similar or identical to the previous embodiment are marked with the same reference numerals, and the descriptions thereof will not be repeated.

The coupling assembly 4' includes a receiving part 5', a retainer element 6', a pressure element 7', and one pin 8'. Referring in addition to FIGS. 32 to 36, the receiving part 5' has an asymmetric accommodation space 54'. The accommodation space 54' has a first portion 54a' that extends between the coaxial bore 51 and a seat portion 54b' that has a spherical segment shape with a limited length in a circumferential direction. The size of the spherical section of the seat portion 54b' matches the size of a lower portion of the head 3. Hence, the spherical section 54b' provides a partial spherical seat for the head 3. From the spherical section 54b', a compartment 54d' extends from a bottom shoulder 54c' up to a height that is above (i.e., closer to the top end 5a than) a bottom of the U-shaped recess 52. The compartment 54d' enlarges the accommodation space asymmetrically with respect to the central axis C, so that at one of the legs 52a, there is an enlarged space for receiving the retainer element 6' according to the second embodiment. The lower edge 54c' of the compartment 54d' serves as a support for supporting the retainer element 6', as shown in FIG. 31. The accommodation space 54' of the receiving part 5' has a greater diameter at a region of the compartment 54d' than at a region of the spherical section 54b'. In addition, a transverse pin hole 56' for receiving the pin 8' and a circumferential extending undercut portion 57' above the pinhole 56' are provided in the receiving part 5'.

Figure 39:
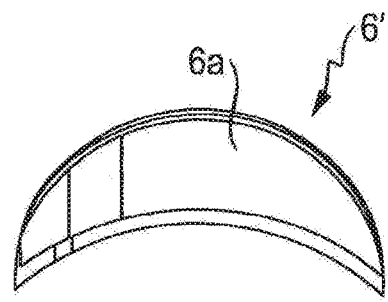
FIG. 39 shows a top view of the retainer element of FIGS. 37 and 38.
Figure 40:
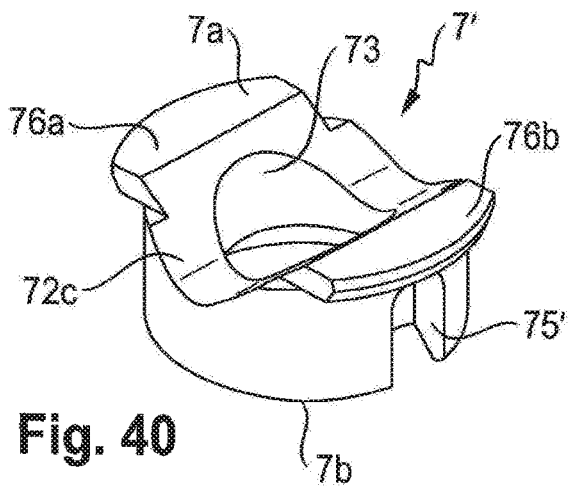
FIG. 40 shows a perspective view from above of a pressure element of the polyaxial bone anchoring device according to the second embodiment.
Figure 41:
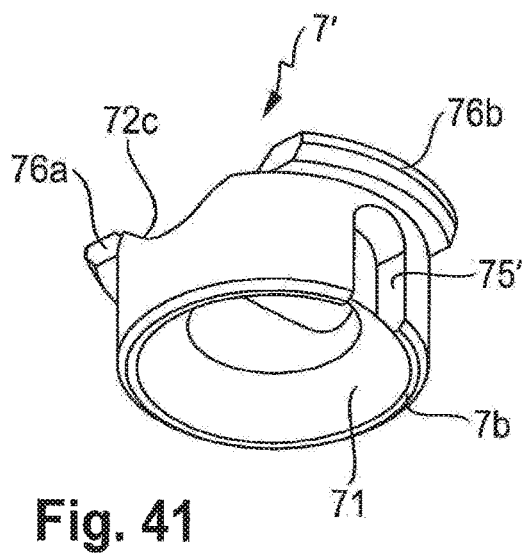
FIG. 41 shows a perspective view from a bottom of the pressure element of FIG. 40.
Figure 42:
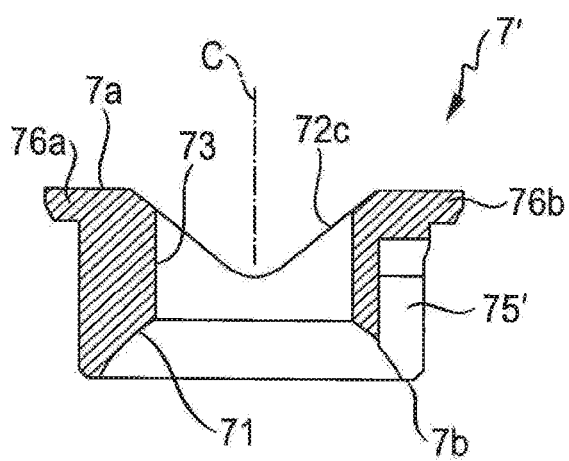
FIG. 42 shows a cross-sectional view of the pressure element of FIGS. 40 and 41, the cross-section being taken in a plane perpendicular to an axis of an inserted rod.

The retainer element 6' includes a main portion 61' that has an outer cylinder segment-shaped contour 61a and an inner spherical segment-shaped contour 61b, which together resemble a sickle or a crescent shape from a top view (for example, as seen in FIG. 39). The main portion 61' of the retainer element 6' has a height and a width in a circumferential direction that allows the main portion 61' to encompass at least a portion of the spherical head 3. The main portion 61' fits into a lower portion of the compartment 54d', such that the main portion 61' can rest on the support 54c'. From the main portion 61', a spring portion 66' extends upward towards the top end 6a. The spring portion 66' is shaped similar to a snake spring, and has a sickle-shaped or crescent-shaped contour from a top view, as shown in FIG. 39. A number and the lengths of, as well as the distances between, the substantially vertical sections 67' and the substantially horizontal sections 68' that form the meandering design of the spring portion 66' can be adjusted or selected to achieve a desired resiliency and spring force. The retainer element 6' is configured to be inserted into the compartment 54d'. Once the retainer element 6' is inserted into the compartment 54d', the retainer element 6' extends in an oblique or tilted manner relative to the central axis C of the coupling assembly 4', as depicted in FIG. 31.

The pressure element 7' includes at a top end 7a two lateral collar portions 76a, 76b that extend from a V-shaped groove 72c beyond an outer diameter of a cylindrical body of the pressure element 7'. The collar portions 76a, 76b have an outer size such that the collar portions 76a, 76b can extend into the undercut portion 57' provided above the pin hole 56' in the receiving part 5'. Below one of the collar portions, e.g., the collar portion 76b in the embodiment shown, an elongate U-shaped recess 75' is provided that is open towards a bottom end 7b of the pressure element 7'. The U-shaped recess 75' serves for receiving a portion of the pin 8' therein.

Referring in particular to FIG. 31, the coupling assembly may be pre-assembled such that the retainer element 6' is inserted into the receiving part 5' from the top end 5a and through the coaxial bore 51, until the retainer element 6' is seated in the compartment 54d', and the main portion 61' rests on the support 54c'. The height of the compartment 54d' is such that the spring portion 66' may be slightly pre-tensioned when the retainer element 6' is placed into the compartment 54d'. The inner spherical surface 61b extends into the accommodation space 54' and forms a second portion of a seat for the head 3, that encompasses a portion of the head 3 on a side opposite a side of the spherical seat 54b'.

The pressure element 7' is also inserted from the top end 5a in a manner such that the collar portions 76a, 76b are aligned with the rod receiving channel 52 of the receiving part 5'. Then the pressure element 7' is moved downward until the collar portions 76a, 76b reach the undercut portion 57'. In this position, the pressure element 7' can be rotated so that the V-shaped groove 72c is aligned with the channel 52 of the receiving part 5', and the collar portions 76a, 76b still extend into the undercut portion 57'. Thereafter, the pin 8' is inserted through the pin hole 56' until its front portion extends into the U-shaped recess 75' of the pressure element 7'. The pin 8' prevents rotation of the aligned pressure element 7'.

In use, the head 3 enters through the lower opening 55' and moves the retainer element 6' upward, thereby compressing the spring 66' that moves or pushes against the upper wall of the oblique compartment 54d'. The pressure element 7' is also pushed upward by the head 3 until its free end surface 7a, provided on the collar portions 76a, 76b, abuts against an upper surface of the undercut 57'. When the head 3 presses against the spherical recess 71 of the pressure element 7', the spring force of the spring portion 66' causes the retainer element 6' to snap over or past the portion of the head 3 with the largest diameter E until the main portion 61' of the retainer element 6' rests on the support 54c' in the receiving part 5'. In this position, the head 3 can no longer be removed from the receiving part 5'.

Further modifications of the embodiments may also be contemplated. For example, for the bone anchoring element, various different kinds of anchoring elements can be used and combined with the receiving parts. Such anchoring elements may be, for example, screws with different lengths, screws with different diameters, cannulated screws, screws with different thread forms, nails, hooks, etc. For some anchoring elements, the head and the shank may also be separate parts that can be connected to each other.

Other possible modifications of the receiving part may include, for example, instead of having a U-shaped recess being perpendicular to the central axis, a recess for the rod may be inclined, open to the side of the receiving part, or may be realized in the form of a closed channel. Other kinds of locking devices, including outer nuts, outer caps, bayonet locking devices, or others are also possible. In particular, a two-part locking device that includes a first locking element that exerts pressure via the pressure member only onto the head and a second locking element that exerts pressure only onto the rod to lock the head and the rod independently, may also be used. In some embodiments, the inner surface portion of the pressure member that contacts the head, may not necessarily be spherically-shaped. The inner surface portion may instead have any other shape that is suitable to exert pressure onto the head.

In some embodiments, instead of a pin that extends through a pin hole at the receiving part and engages an elongate recess provided at the pressure element, other retaining mechanisms can be used that help retain the pressure member in alignment with the receiving part and inhibit or restrict the pressure member from moving out through the top end of the receiving part.

The head of the bone anchoring element need not be rotationally symmetric. For example, the head may have two opposite flat surface portions between two spherically-shaped outer surface portions, so as to achieve pivoting in only one plane.

The spring portion or portions of the retainer element may have other shapes that ensure sufficient length of the spring portion in an axial direction and sufficient spring force. For example, a helical spring may also be contemplated.

Instead of a slit ring, a plurality of vertically extending slits or a combination of substantially vertically and substantially horizontally extending slits may instead be provided.

The seat for the slit ring and the outer surface of the slit ring also need not be conical. Any shape that provides for safe holding of the slit ring in the receiving part may also be contemplated, such as, for example, a spherical shape.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. A bone anchoring device for coupling a rod to a bone, the bone anchoring device comprising:
   a bone anchoring element comprising a shank for anchoring to bone and a head;
   a receiving part having a first end, a second end, a central axis extending through the first end and second end, a recess at the first end for receiving the rod, and an accommodation space for accommodating the head of the bone anchoring element;
   a pressure element positionable at least partially in the accommodation space to exert pressure on the head; and
   a retainer element that is separable from the pressure element and positionable at least partially in the accommodation space, wherein the retainer element comprises a spring;
   wherein when the head, the pressure element, and the retainer element are in the receiving part, the spring is located circumferentially on one side of the head without extending to an opposite side of the head and has at least a portion that is located at a same axial height in the receiving part as at least part of the head, with the spring being configured to expand and compress at least partially in a radial direction to hold a position of the head in the receiving part.

2. The bone anchoring device of claim 1, wherein the spring is slightly inclined with respect to the central axis.

3. The bone anchoring device of claim 1, wherein the retainer element is directly engageable with both the pressure element and the head in the receiving part.

4. The bone anchoring device of claim 1, wherein the spring extends in an oblique manner within an enlarged compartment of the receiving part.

5. The bone anchoring device of claim 1, wherein the pressure element is insertable into the receiving part from the first end by rotating the pressure element relative to the receiving part.

6. The bone anchoring device of claim 1, further comprising a pin that is configured to extend laterally into the receiving part to engage the pressure element.

7. The bone anchoring device of claim 6, wherein the pin engages a vertically extending groove formed in a side surface of the pressure element to restrict rotation of the pressure element in the receiving part.

8. The bone anchoring device of claim 6, wherein the pin is located circumferentially on the opposite side of the head from where the spring is located.

9. The bone anchoring device of claim 6, wherein the spring and the pin are configured to remain spaced apart from one another in the receiving part.

10. The bone anchoring device of claim 6, wherein at least part of the pin is held in a transverse hole in the receiving part.

11. The bone anchoring device of claim 1, wherein the receiving part is pivotable relative to the bone anchoring element such that an angle between the central axis of the receiving part and a shank axis of the bone anchoring element is adjustable.

12. The bone anchoring device of claim 11, wherein the shank axis is pivotable to a greater maximum angle in a first radial direction relative to the central axis of the receiving part than in a different second radial direction relative to the central axis.

13. A bone anchoring device for coupling a rod to a bone, the bone anchoring device comprising:
- a bone anchoring element comprising a shank for anchoring to bone and a head;
- a receiving part having a first end, a second end, a central axis extending through the first end and second end, a recess at the first end for receiving the rod, and an accommodation space for accommodating the head of the bone anchoring element;
- a retainer element engageable with the head when the head is in the accommodation space; and
- a pressure element that is separable from the retainer element and positionable at least partially in the accommodation space to directly exert pressure on the head;
- wherein when the pressure element is in the receiving part at a first position, the head is insertable into the accommodation space of the receiving part; and
- wherein when the head and the pressure element are in the receiving part, the retainer element is configured to directly engage the head to prevent removal of the head from the receiving part while the pressure element remains at the first position.

14. The bone anchoring device of claim 13, wherein the first position of the pressure element is an uppermost position of the pressure element relative to the receiving part that is closest to the first end of the receiving part.

15. The bone anchoring device of claim 13, wherein the retainer element is separable from the receiving part.

16. The bone anchoring device of claim 13, wherein when the head is in the receiving part, the retainer element is configured to directly engage the head to exert a pressure on the head directed towards the first end of the receiving part.

17. The bone anchoring device of claim 16, wherein the retainer element is movable at least partially in a radial direction, while another surface of the receiving part that faces at least partially towards the first end of the receiving part and whose radial position relative to the central axis remains constant forms a seat for the head.

18. The bone anchoring device of claim 13, wherein when the head and the pressure element are in the receiving part, the pressure element is only configured to exert pressure directed towards the second end of the receiving part without exerting pressure directed towards the first end of the receiving part onto the head.

19. The bone anchoring deice of claim 13, wherein a stop is provided for the pressure element to restrict movement of the pressure element towards the first end of the receiving part when the pressure element is in the receiving part.

20. The bone anchoring device of claim 13, wherein when the head is in the receiving part, the retainer element is configured to frictionally engage the head to restrict angular movement between the head and the receiving part while the pressure element remains at the first position.

* * * * *

UNITED STATES PATENT AND TRADEMARK OFFICE
CERTIFICATE OF CORRECTION

PATENT NO. : 11,617,608 B2
APPLICATION NO. : 16/905313
DATED : April 4, 2023
INVENTOR(S) : Lutz Biedermann It is certified that error appears in the above-identified patent and that said Letters Patent is hereby corrected as shown below:

In the Claims

Column 14, Line 31, Claim 19    Delete "deice" and
Insert -- device --

Signed and Sealed this
Twentieth Day of June, 2023

Katherine Kelly Vidal
*Director of the United States Patent and Trademark Office*